United States Patent [19]

Cullinan

[11] Patent Number: 5,439,923

[45] Date of Patent: Aug. 8, 1995

[54] METHOD OF INHIBITING SEBORRHEA AND ACNE

[75] Inventor: George J. Cullinan, Trafalgar, Ind.

[73] Assignee: Eli Lilly and Company, Indianapolis, Ind.

[21] Appl. No.: 170,970

[22] Filed: Dec. 21, 1993

[51] Int. Cl.⁶ ......................................... A61K 31/445
[52] U.S. Cl. .................................................. 514/324
[58] Field of Search ....................................... 514/324

[56] References Cited

U.S. PATENT DOCUMENTS

| | | | |
|---|---|---|---|
| 4,133,814 | 1/1979 | Jones et al. | 260/326.55 |
| 4,380,635 | 4/1983 | Peters | 546/202 |
| 4,418,068 | 11/1983 | Jones | 424/267 |
| 5,075,321 | 12/1991 | Schreiber | 514/317 |

FOREIGN PATENT DOCUMENTS

WO93/10113  5/1993  Japan .
WO93/1074   6/1993  WIPO .

OTHER PUBLICATIONS

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am Soc. Bone & Min. Res., Tampa, Sep. 18-22, 1993.

Bryant et al. "Raloxifene is a Tissue Specific Estrogen Agonist", Am Soc. Bone & Min. Res., Tampa, Sep. 18-22, 1993.

Frolick et al., "In Vivo and In Vitro Metabolism of Raloxifene", Am. Soc. Bone & Min. Res., Tampa, Sep. 18-22, 1993.

Glasebrook et al., "Multiple Binding Sites for the Anti-estrogen Raloxifene", Am Soc. Bone & Min. Res., Tampa, Sep. 18-22, 1993.

Hock et al., "Combination of Raloxifene and Human Parathyroid Hormone 1-34; Increased Femur Bone Mass in Young Ovariectomized (OVX) Rats", Am. Soc. Bone & Min. Res., Tampa, Sep. 18-22, 1993.

Sato et al., "DEXA Analysis of Raloxifene Effects on the Bones From Ovariectomized Rats", Am. Soc. for Bone and Min. Res., Tampa, Sep. 18-22, 1993.

Yang et al., "Raloxifene an Anti-Estrogen, Simulates the Effects of Estrogen in Inhibiting Bone Resorption Through Regulating TGFB-3 Expression in Bone;", Am Soc. for Bone and Min. Res., Tampa, Sep. 18-22, 1993.

(List continued on next page.)

*Primary Examiner*—Zohreh Fay
*Attorney, Agent, or Firm*—James J. Sales; Gerald V. Dahling

[57] ABSTRACT

A method of inhibiting acne or seborrhea comprising administering to a human in need of treatment an effective amount of a compound having the formula

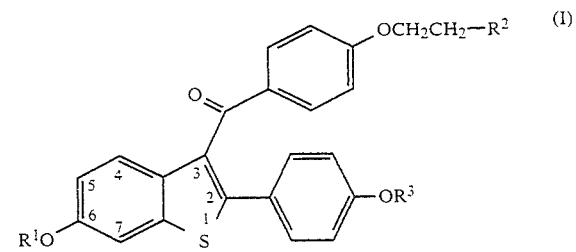

wherein $R^1$ and $R^3$ are independently hydrogen, —$CH_3$,

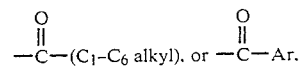

wherein Ar is optionally substituted phenyl;

$R^2$ is selected from the group consisting of pyrrolidine, hexamethyleneamino, and piperidino; or a pharmaceutically acceptable salt of solvate thereof.

5 Claims, No Drawings

OTHER PUBLICATIONS

Black et al., "Distinct, Structure-Related Profiles of Estrogenic and Anti-Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109:1981, 987–989.

Black, L. J., "Biological Actions and Binding Properites of a New Estrogen Antagosist LY117018," In: Homone Antagonists, 129–82, 1982 (M. K. Agarwal ed.) Walter de Gruyter and Co., Berlin New York.

Black et al., LY156758: A Unique Antiestrogen Displaying High Affinity for Estrogen Receptors, Negligible Estrogenic Activity and Near-Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H-LY139481 Distribution In Vivo. Sixty-fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983, 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro-2(4–methoxyphenyl)-1-napthalenyl] [4–[2-pyrrolidinyl) ethoxyl]-phenyl] methanone, methanesulfonic acid salt, Journal of Medicinal Chemistry, 22;1979, 962–966.

Black et al., Antiestrogens 2. Structure Activity Studies in a Series of 3–Aroyl-2-arylbenzo[b]thiophene Derivatives Leading to [6–Hydroxy-2-(4-hydroxyphenyl)-benzo[b]thien-3-yl[4-[2-(1-piperidinyl)ethoxy]--phenyl]methanone Hydrochloride (LY156758), a Remarkably Effective Estrogen Antagonist with Only Minimal Intrinsic Estrogenicity, J. Med. Chem. 27(8), 1984, 1057–1066.

METHOD OF INHIBITING SEBORRHEA AND ACNE

BACKGROUND OF THE INVENTION

Acne and seborrhea are two general classes of skin diseases which are marked by an abnormal function (usually hyperactivity) of the sebaceous glands in the skin. The subject of this invention is the use of compounds to inhibit acne and seborrhea.

Acne vulgaris is a disease of the pilosebaceous unit in the skin and is chronic and inflammatory in nature. It is characterized by comedos (blackheads), papules, pustules, cysts, and nodules. The areas of the body most commonly affected by the disease are those which have the most sebaceous glands, i.e., the face, neck, back, and chest. Acne is very common disease in both men and women and usually appears at the beginning of puberty. Although, the disease is usually mild and resolves itself by the time most people reach their midtwenties, it can in many instances be disfiguring and a source of great physiological distress. In some extreme cases, acne can be the source of severe infection and even life-threatening.

The etiology and pathogenesis of the disease begins with cohesive hyperkeratosis in which cornified cells adhere and block the follicular canal between the sebaceous gland and the surface of the skin. The sebaceous gland under hormonal control (testosterone and dihydrotestostrone) are stimulated to enlarge and produce increasing amounts sebaceous secretions (principally in the form of triacylglycerols). These sebaceous secretions are trapped in the blocked, follicular canal and build up to form a closed comedo. At this stage, common, indigenous skin bacteria (principally, *Propionibacterum Acnes*) begin to metabolize the triacylglycerols to free fatty acids. These liberated fatty acids are inflammatory and results in the formation of a papule. This papule is often raised and is typical of an inflammatory lesion, i.e., red, edematous, and painful. The papule may continue to expand and rupture the follicle wall, thus forming a pustule or cyst. The pustule stage is very painful and unsightly and is often a site for secondary infection by opportunistic bacteria such as Staphofius. The pustules and cysts often lead to the scarring and disfigurement seen in severe cases of acne.

There are several drugs available for the treatment of acne. For mild cases, benzoyi peroxide is used and is often moderately effective. Benzoyl peroxide is thought to work by inhibiting cohesive hyperkeratosis and by suppressing *P. Aches*. although benzoyl peroxide is effective in mild cases of acne, it suffers from several drawbacks: first, it must be applied topically and does not always penetrate to the pilosebaceous unit where the acne lesion initiates, second, it can cause skin irritation which can exacerbate the disease. Another moderately effective drug is vitamin A (retenoic acid, Retin-A) which is used topically. Vitamin A inhibits cohesive hyperkeratosis; however, being a topical preparation it suffers from some of the same drawbacks as benzoyl peroxide and in addition it can cause a deterioration of the protective stratum corneum if used extensively. Yet another group of commonly used drugs for the treatment of acne are antibiotics. These can be used either topically or systemically. The most commonly used antibiotics are tetracyclines and erythromycin and to a lesser extent minocycline, ampicillin, clindamycin, trimethoprim, and sulfamethoxazole. These antibiotics inhibit *P. Aches* and other secondary bacterial infections. There are two major drawbacks to the prolonged use of antibiotics for acne; first, the continued long exposure to antibiotics often lead to formation of resistant bacterial strains both in the skin and systemically, and second continued use of antibiotics may lead to sensitization of the patient to the antibiotic. A newer drug used for acne is Isotretinoin (Accutane, 13-cis-retenoic acid). This drug works like vitamin A; however, it can be used systemically. The side-effects of isotretinoin are often: cheiliris, a rise in serum triglycerides, elevated sedimentation rates, and most importantly, isotretinoin is a teratogen in humans and therefore cannot be used if there is a question of pregnancy during treatment. All of the above drugs have some positive effect in the treatment of acne, but each has its limiting side-effects.

Hormonal therapy is also effective for the treatment of acne in women. In many cases, the administration of estrogens has a positive effect in treating acne. Estrogens counteract the effect endogenous androgens and therefore, decrease sebaceous excretion. However, since the use of unopposed estrogen administration in women with a uterus poses the potential for the development of endometrial cancer, a cyclic therapy of estrogen and a progestin are used for the treatment of acne. Typically, women are prescribed the normal birth control protocols for acne treatment. Although, these protocols are often effective for acne, in many cases these regiments contain progestins which have significant androgenic activity. This androgenic activity exacerbates the disease. Additionally, it is well known that progestinal agents are the cause of many negative, psychological side-effects. Clearly, a better hormonal agent would be beneficial.

Seborrhea or seborrheic dermatitis is another group of skin diseases thought to be associated with abnormal function of the sebaceous glands. It occurs in areas where there are large numbers of sebaceous glands and is characterized by flaking of the skin and red, mildly inflammatory patches. Seborrhea is most common in the hair (a form of dandruff), scalp margins, eyebrows, naso-labial folds, external ear canals, postier auricular fold, and presternal area. Generally, mild seborrhea is controlled by topical medication such as glucocorticoids and LDH in Nivea oil. However, more severe cases are more difficult to control.

SUMMARY OF THE INVENTION

This invention provides methods for inhibiting acne or seborrhea comprising administering to a human in need of treatment an effective amount of a compound of formula I

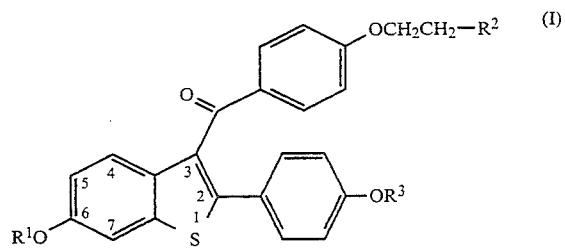

wherein $R^1$ and $R^3$ are independently hydrogen, —$CH_3$,

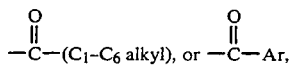

wherein Ar is optionally substituted phenyl;

$R^2$ is selected from the group consisting of pyrrolidino, hexamethyleneimino, and piperidino; and pharmaceutically acceptable salts and solvates thereof.

DETAILED DESCRIPTION OF THE INVENTION

The current invention concerns the discovery that a select group of 2-phenyl-3-aroylbenzothiophenes (benzothiophenes), those of formula I, are useful for inhibiting acne or seborrhea. The methods of treatment provided by this invention are practiced by administering to a human in need of a dose of a compound of formula I or a pharmaceutically acceptable salt or solrate thereof, that is effective to inhibit acne or seborrhea. The term inhibit is defined to include its generally accepted meaning which includes prophylactically treating a human subject to incurring the conditions described, and holding in check and/or treating existing conditions. As such, the present method includes both medical therapeutic and/or prophylactic treatment, as appropriate.

Raloxifene, a compound of this invention wherein it is the hydrochloride salt of a compound of formula 1, $R^1$ and $R^3$ are hydrogen and $R^2$ is 1-piperidinyl, is a nuclear regulatory molecule. Raloxifene has been shown to bind to the estrogen receptor and was originally thought to be a molecule whose function and pharmacology was that of an anti-estrogen in that it blocked the ability of estrogen to activate uterine tissue and estrogen dependent breast cancers. Indeed, raloxifene does block the action of estrogen in some cells; however in other cell types, Raloxifene activates the same genes as estrogen does and displays the same pharmacology, e.g., osteoporosis, hyperlipidemia. As a result, raloxifene has been referred to as an anti-estrogen with mixed agonist-antagonist properties. The unique profile which raloxifene displays and differs from that of estrogen is now thought to be due to the unique activation and/or suppression of various gene functions by the raloxifene-estrogen receptor complex as opposed to the activation and/or suppression of genes by the estrogen-estrogen receptor complex. Therefore, although Raloxifene and estrogen utilize and compete for the same receptor, the pharmacological outcome from gene regulation of the two is not easily predicted and is unique to each.

Generally, the compound may be formulated with common excipients, diluents or carriers, and compressed into tablets, or formulated as elixirs or solutions for convenient oral administration, administered by the intramuscular or intravenous routes, or administered topically. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. Substituted phenyl includes phenyl substituted once or twice with $C_1$-$C_6$ alkyl, $C_1$-$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, subcrate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonire; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit acne or seborrhea in a non-topical administration, according to this invention will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need of treatment from once to about three times each day, or more often as needed to effectively treat the symptoms.

For topical administration, the compounds may be formulated as is known in the art for direct application to an area. Conventional forms for this purpose include ointments, lotions, pastes, jellies, sprays, and aerosols. The percent by weight of a compound of the invention present in a topical formulation will depend on various factors, but generally will be from 0.5% to 95% of the total weight of the formulation, and typically 1–25% by weight.

The compositions can take the form of an aqueous or anhydrous solution or dispersion, or alternatively the form of an emulsion or suspension.

These compositions can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$–$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carob gum or gum arabic, or alternatively polyethylene glycols, bentones and montmorillonites, and the like.

These compositions according to the invention can also contain, in combination, other active agents such as retinoic derivatives, antibacterial agents, antiinflammatories, and steroids such as pregnenolone. Examples of such agents include benzoyl peroxide, tetracyclins, erythromycin, minocycline, clindamycin, ampicillin, trimethoprim, sulfamethoxazole, vitamin A, and isotretinoin; for seborrhea; LHD in Nivea oil and glucorticoiods.

It is possible to add, if necessary, an adjuvant chosen from antioxidants, surfactants, other preservatives, film-forming, keratolytic or comedolytic agents, perfumes and colourings.

For example, among antioxidants, t-butylhydroquinone, butylated hydroxyanisole, butylated hydroxytoluene and $\alpha$-tocophrol and its derivatives may be mentioned.

The galenical forms chiefly conditioned for topical application take the form of creams, milks, gels, dispersions or microemulsions, lotions thickened to a greater or lesser extent, impregnated pads, ointments or sticks, or alternatively the form of aerosol formulations in spray or foam form or alternatively in the form of a cake of soap.

FORMULATIONS

In the formulations which follow, "Active ingredient" means a compound of formula I.

Formulation 1: Gelatin Capsules

Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of the compound of formula 1 wherein $R^2$ is piperidino, (raloxifene), that have been made include those shown below:

Formulation 2: Raloxifene capsule

| Ingredient | Quantity (mg/capsule) |
|---|---|
| Raloxifene | 1 |
| Starch, NF | 112 |
| Starch flowable powder | 225.3 |
| Silicone fluid 350 centistokes | 1.7 |

Formulation 3: Raloxifene capsule

| Ingredient | Quantity (mg/capsule) |
|---|---|
| Raloxifene | 5 |
| Starch, NF | 108 |
| Starch flowable powder | 225.3 |
| Silicone fluid 350 centistokes | 1.7 |

Formulation 4: Raloxifene capsule

| Ingredient | Quantity (mg/capsule) |
|---|---|
| Raloxifene | 10 |
| Starch, NF | 103 |

-continued

| Ingredient | Quantity (mg/capsule) |
|---|---|
| Starch flowable powder | 225.3 |
| Silicone fluid 350 centistokes | 1.7 |

Formulation 5: Raloxifene capsule

| Ingredient | Quantity (mg/capsule) |
|---|---|
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
|---|---|
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

Formulation 7: Tablets

| Ingredient | Quantity (mg/tablet) |
|---|---|
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 500°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

Formulation 8: Suspensions

| Ingredient | Quantity (mg/5 ml) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |

-continued

| Ingredient | Quantity (mg/5 ml) |
|---|---|
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

The following composition is prepared:

Formulation 9

| Ingredient | Quantity (mg/5 ml) |
|---|---|
| Hydroxypropylcellulose | 1.5 g |
| Active Ingredient | 1.5–30 g |
| Isopropanol qs | 100 g |

Formulation 10

The following composition is prepared:

| Ingredient | Quantity (mg/5 ml) |
|---|---|
| Hydroxypropylcellulose | 1.5 g |
| Ethyl lactate | 15.0 g |
| Active Ingredient | 1.5–30 g |
| Isopropanol qs | 100 g |

Formulation 11

The following composition is prepared:

| Ingredient | Quantity (mg/5 ml) |
|---|---|
| Hydroxypropylcellulose | 1.0 g |
| Butylated hydroxytoluene | 0.02 g |
| Active Ingredient | 1.5–25 g |
| Ethanol qs | 100 g |

Formulation 12

The following composition is prepared:

| Ingredient | Quantity (mg/5 ml) |
|---|---|
| Hydroxypropylcellulose | 1.5 g |
| Butylated hydroxytoluene | 0.01 g |
| $C_8$–$C_{12}$ fatty acid triglycerides | 10.0 g |
| Active Ingredient | 1.5–30 g |
| Isopropanol qs | 100 g |

Formulations 9–12 take the form gels, and are intended for the topical treatment of acne.

Formulation 13

The following composition is prepared:

| Ingredient | Quantity (mg/5 ml) |
|---|---|
| Isopropanol | 46.0 g |
| Active Ingredient | 1.0–15 g |
| $C_8$–$C_{12}$ fatty acid triglycerides | 49.0 g |

Formulation 14

The following composition is prepared:

| Ingredient | Quantity (mg/5 ml) |
| --- | --- |
| Ethanol | 69.0 g |
| Ethyl lactate | 10.0 g |
| Active Ingredient | 1.5–20 g |
| $C_8$–$C_{12}$ fatty acid triglycerides | 30.0 g |

Formulation 15

The following composition is prepared:

| Ingredient | Quantity (mg/5 ml) |
| --- | --- |
| Isopropanol | 47.0 g |
| Acetone | 10.0 g |
| Ethyl lactate | 10.0 g |
| Active Ingredient | 1–15 g |
| $C_8$–$C_{12}$ fatty acid triglycerides | 30.0 g |

Formulation 16

The following composition is prepared:

| Ingredient | Quantity (mg/5 ml) |
| --- | --- |
| Ethanol | 95.08 g |
| Butylated hydroxytoluene | 0.02 g |
| Active Ingredient | 1.5–25 g |

Formulations 13, 14, 15, and 16 take the form of a lotion.

Formulation 17

The following composition is prepared:

| Ingredient | Quantity (mg/5 ml) |
| --- | --- |
| White vaseline | 50.0 g |
| Liquid paraffin | 15.0 g |
| Refined paraffin wax | 32.0 g |
| Active ingredient | 1–20 g |

Formulation 18

The following composition is prepared:

| Ingredient | Quantity (mg/5 ml) |
| --- | --- |
| White vaseline | 50.0 g |
| Liquid paraffin | 13.0 g |
| Refined paraffin wax | 32.0 g |
| Active Ingredient | 1–20 g |

Formulations 17 and 18 takes the form of a stick.

ASSAYS

Assay 1

Each of from between two and twenty patients selected for the clinical evaluation is placed in a comfortable environment, i.e., comfortable temperature, humidity, lighting, etc. These patients have refrained from strenuous exercise and consumption of spicy foods for the twelve hours prior to the evaluation. An area of the body which contains a large number of sebaceous glands affected by seborrhea or acne, such as the forehead, is wiped with a gauze pad to remove accumulated lipids. A patch of the skin is taped off, forming a rectangle sized 2.5 by 1.8 cm. A pad of cigarette paper or other suitable absorbent material sized 2.5 by 1.8 cm is placed on the test area of the skin. The absorbent material must have first been defatted with ether prior to the placement on the test area to remove background lipids. The pad is the held in place with a bandage. After fifteen minutes the pad is replaced with a fresh pad (test pad). This procedure removes the background lipids in the skin so the true rate of lipid production by the sebaceous glands may be determined. The test pad is left in place for three to six hours and then removed. The test pad is then extracted with ether to remove the lipids and the ether evaporated. The residual lipids are then weighed. The result is expressed as the number of sebaceous lipids (mg) per 10 cm² per hour. The patient then takes either 30–400 mg/day of the active ingredient by the oral route, or applies a topical formulation containing 5–20% by weight of the active ingredient daily, both for three to nine weeks. The above described test pad methodology is repeated several times throughout administration of the active ingredient to monitor progress. This assay may also be performed on animals to verify utility. A positive effect is reflected by a decrease of the rate of sebaceous gland lipid production.

Assay 2

Between two and twenty patients are enrolled in this clinical protocol and are initially evaluated by direct observation of the skin and lesions thereon. This is done by choosing one cm² sections of affected skin and the number and type of lesion (comedos, seborrehic lesions, etc.) is noted. The areas normally used are the cheeks, scalp or back. The patient then takes either 30–400 mg/day of the active ingredient by the oral route, or applies a topical formulation containing 5–20% by weight of the active ingredient daily, both for three to nine weeks The areas of the skin being evaluated are checked during the period of administration. Care must be taken to evaluate the same areas and in order to accomplish this a small mark or marks may be made on the skin by a permanent marker. A positive result is reflected by a reduction in the number and/or severity of the lesions in the monitored areas of the skin.

Utility of the compounds described herein is exhibited by the positive results observed in one or both of the above assays.

We claim:

1. A method of inhibiting acne or seborrhea comprising administering to a human in need of treatment an effective amount of a compound having the formula

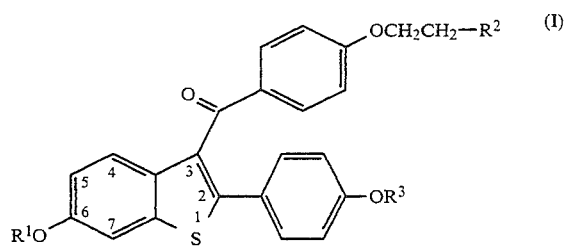

wherein $R^1$ and $R^3$ are independently hydrogen, —$CH_3$,

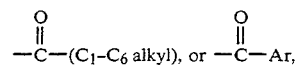

wherein Ar is optionally substituted phenyl;

R² is selected from the group consisting of pyrrolidine, hexamthylenemino, and piperidino; or a pharmaceutically acceptable salt of solvate thereof.

2. The method of claim 1 wherein said compound is the hydrochloride salt thereof.

3. The method of claim 1 wherein said compound is

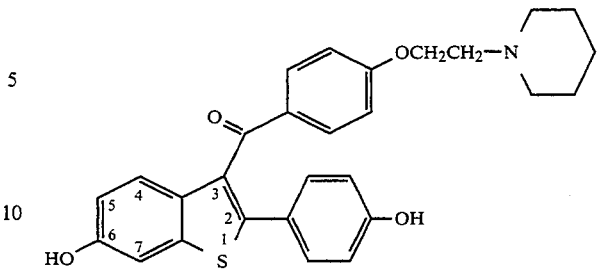

or its hydrochloride salt.

4. A topical formulation comprising a compound of claim 1 and one or more topical formulation additives.

5. The method of claim 4 where said formulation comprises at least one other active agent.

* * * * *

UNITED STATES PATENT AND TRADEMARK OFFICE
CERTIFICATE OF CORRECTION

PATENT NO. : 5,439,923

DATED : August 8, 1995

INVENTOR(S) : George J. Cullinan

It is certified that error appears in the above-indentified patent and that said Letters Patent is hereby corrected as shown below:

Column 11, line 6, "hexamthylenemino" should read --hexamethyleneimino--.

Column 12, line 17, delete "method" and insert therefor --formulation--.

Signed and Sealed this

Twenty-first Day of November, 1995

Attest:

BRUCE LEHMAN

*Attesting Officer*   *Commissioner of Patents and Trademarks*